United States Patent [19]

Love et al.

[11] Patent Number: 4,778,906

[45] Date of Patent: Oct. 18, 1988

[54] PROCESS FOR THE PREPARATION OF ZINC DIALKYLDITHIOPHOSPHATE

[75] Inventors: Doris Love, Fishkill; Carmen M. Cusano, Poughkeepsie; Joseph B. Biasotti, Lagrangeville, all of N.Y.; Harold S. Magaha, Saint Peters, Mo.

[73] Assignee: Texaco Inc., White Plains, N.Y.

[21] Appl. No.: 901,859

[22] Filed: Aug. 28, 1986

[51] Int. Cl.$^4$ ............................................... C07F 3/06
[52] U.S. Cl. ............................................ 556/25; 556/2
[58] Field of Search .................................. 556/25, 2

[56] References Cited

U.S. PATENT DOCUMENTS

| | | | |
|---|---|---|---|
| 1,944,274 | 1/1934 | Salzberg | 556/2 |
| 2,932,614 | 4/1960 | Lynch et al. | 556/25 X |
| 4,244,827 | 1/1981 | Michaelis et al. | 556/25 X |
| 4,400,283 | 8/1983 | Horodysky et al. | 556/25 X |
| 4,450,096 | 5/1984 | Horodysky | 556/25 X |
| 4,460,511 | 7/1984 | Boston | 556/25 X |

*Primary Examiner*—Paul F. Shaver
*Attorney, Agent, or Firm*—Robert A. Kulason; James J. O'Loughlin; Robert B. Burns

[57] ABSTRACT

A process for preparing a zinc dialkyldithiophosphate which comprises reacting phosphorus pentasulfide with an aliphatic monohydric alcohol in the presence of a hydrocarbyl polyol followed by a reaction with a basic zinc salt to produce a stabilized zinc dialkyldithiophosphate is provided.

1 Claim, No Drawings

PROCESS FOR THE PREPARATION OF ZINC DIALKYLDITHIOPHOSPHATE

BACKGROUND OF THE INVENTION

Lubricants, including lubricating oils and greases, are used in a variety of applications in which the lubricant is in contact with or admixed with air often at elevated temperatures and/or under severe operating conditions. Some of these conditions promote thermal and oxidative degradation of the product. This degradation or breakdown is usually manifested by deterioration in appearance, physical properties or in the performance of the lubricant. For example, the formation and deposition of varnishes and sludge on engine surfaces is primarily due to oxidation and polymerization occurring in the lubricating oil. These deposits are undesirable since they contribute to wear and corrosion of the engine surfaces.

Particularly effective lubricant additives because they exhibit desirable anti-oxidant and detergent properties are the zinc salts of esters of dithiophosphoric acid. These compounds are prepared by reacting alkyl or alkaryl compounds with phosphorus pentasulfide and thereafter neutralizing the resulting dithiophosphoric acid with a zinc salt such as zinc oxide to produce the zinc dialkyldithiophosphate additive. While the basic method and variations thereto are well known, the additives produced are not entirely satisfactory. Under conditions of extreme stress, the zinc dialkyldithiophosphate will undergo degradation resulting in the production of sulfides which will pass through the combustion and exhaust system of the vehicle with undesirable effects.

The object of this invention is to provide a novel zinc dialkyldithiophosphate which is more stable under engine operating conditions.

DISCLOSURE STATEMENT

U.S. Pat. No. 3,686,243 discloses a process for the preparation of zinc dialkyldithiophosphate wherein the reaction is conducted in a heptane solvent in which specific mole ratios of water are employed in the process. U.S. Pat. No. 4,400,283 discloses a process for producing zinc dialkyldithiophosphates wherein a metal salt of a partially phosphosulfuride polyolbased hydroxol-containing ester is employed.

U.S. Pat. No. 3,720,613 discloses a stabilized mixture of zinc dialkyl and zinc dialkylphenoxyethyldithiophosphates.

U.S. Pat. No. 4,450,096 discloses a zinc dialkyldithio process in which a mixture of $1,2$—$C_{15}C_{18}$ alkane diols are employed.

The disclosure of the foregoing patents are incorporated herein by reference.

SUMMARY OF THE INVENTION

It has now been discovered that the use of a small amount of hydrocarbyl polyol during the preparation of a zinc dialkyldithiophosphate will result in the production of a substantially more stable lubricant additive. The products produced exhibit improved volatility and improved anti-oxidant properties making them highly effective for a variety of lubricant applications including use in a crankcase lubricating oil composition. There is a sharply reduced breakdown or generation of sulfide products in the engine as well as release of sulfides into the atmosphere from the novel zinc dialkyldithiophosphate of the invention.

DESCRIPTION OF THE PREFERRED EMBODIMENTS

Methods for preparing dialkyldithiophosphoric acids are well known to those skilled in the art. A typical procedure involves heating a mixture of heptane solvent and phosphorus pentasulfide ($P_2S_5$) and adding thereto under agitation an alkanol or a mixture of alkanols. Heating is continued until the reaction is completed whereupon the distillate is removed and the remaining mixture cooled and filtered to remove residual phosphorus pentasulfide and recovery of the dialkyldithiophosphoric acid.

In the second step of the preparation, a basic zinc salt is employed to effect neutralization of the dialkyldithiophosphoric acid. Zinc salts such as zinc oxide, zinc hydroxide, zinc carbonate and the like or mixtures of the same, can be employed to produce the zinc dialkyldithiophosphate product.

In accordance with the present invention, a minor amount of hydrocarbyl polyol in admixture with the monohydric alcohol reactant is employed in the reaction with phosphorus pentasulfide to effect the production of the dialkylthiophosphoric acid. In general, the amount of the hydrocarbyl polyol may range from about 0.1 to 12 mole percent based on the total moles of alcohol employed in the process. A preferred amount of the hydrocarbyl polyol is from about 0.25 to 6 mole percent, with the most preferred concentration being between 0.5 and 3 mole percent of the hydrocarbyl polyol per 100 mole percent of alcohol reacted; i.e. of the total of monohydric and polyhydric alcohols.

The hydrocarbyl polyol employed for preparing the zinc dialkyldithiophosphate reaction product of the invention is represented by the formula:

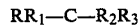

in which R is a methylol or a hydroxyaryl radical having 1 to 8 carbon atoms, or $R_1$ and $R_2$ are hydrogen, a $C_{1-6}$ hydrocarbyl radical or a $C_{1-6}$ hydroxyalkyl radical, and $R_3$ represents a hydroxy radical or a $C_{1-6}$ mono or polyhydroxyalkyl radical.

Examples of specific hydrocarbyl polyols which can be employed in the process of the invention include ethylene gylcol, glycerol, 1,6-hexanediol, 1,4-butanediol, pentaerythritol, and Bisphenol A (4,4-isopropylidinediphenol). Ethylene glycol is the preferred hydrocarbyl polyol for preparing the reaction products of the invention.

It is postulated that the use of a minor amount of the prescribed hydrocarbyl polyol in conjunction with the monohydric alcohol in the reaction with $P_2S_5$ results in the production of a reaction product having some cross-linking. This cross-linking in the final zinc dialkyldithiophosphate substantially stabilizes the additive and imparts enhanced resistance to oxidation and improves volatility characteristics.

The following examples illustrate the practice of this invention.

EXAMPLE 1

222 grams (1.0M) of phosphorus pentasulfide was slowly added over 30 minutes to a stirred mixture of 157.1 grams (1.54M) of methyl isobutylcarbinol, 169 grams (2.82M) of isopropyl alcohol and 2.7 grams (0.044M) of ethylene glycol at 70° C. under a nitrogen atmosphere. This mixture was continuously stirred at 90° C. for 5 hours under a nitrogen blanket and then cooled and filtered. The intermediate dialkyldithiophosphoric acid reaction product had a neutralization number of 214.

The intermediate reaction product from the above step was added to a slurry of 89.5 grams (1.1M) zinc oxide in 400 milliliters of heptane at a temperature not exceeding 66° C. This reaction mixture was stirred at 71° C. for 1.5 hours under nitrogen. The mixture was then heated to reflux temperature and water was removed as an azeotrope as the temperature was increased to 100° C. The mixture was cooled and filtered. The solvent was stripped off and the final product filtered. Analysis of the final reaction product found it to contain: 11.5% zinc, 10.96% P and 22.5% S.

The following examples were prepared using the same procedure described in Example 1 above except for the indicated changes in the specific hydrocarbyl polyol employed and the concentration of this polyol. The comparative example employed no polyol. The resultant zinc dialkyldithiophosphoric acid reaction product was tested for kinematic viscosity. The examples and kinematic viscosity test results are set forth in Table I below.

TABLE I

KINEMATIC VISCOSITIES OF DIOL-POLYOL MODIFIED ZDTPs

| EXAMPLE | MODIFICATION (MOLE % POLYOL) | KIN. VIS @ 100° C., CS. |
|---|---|---|
| 2 (Comparative) | None | 15.4 |
| 3 | 1% BisphenolA | 17.7 |
| 4 | 1% Glycerol | 21.1 |
| 5 | 3% Glycerol | 34.5 |
| 6 | 1% Ethylene glycol | 19.6 |
| 7 | 3% Ethylene glycol | 33.7 |
| 8 | 4% Ethylene glycol | 38.2 |
| 9 | 5% Ethylene glycol | 49.5 |
| 10 | 6% 1,6-Hexanediol | 32.3 |
| 11 | 12% 1,6-Hexanediol | 144.4 |
| 12 | 6% trimethylolpropane | 93.8 |
| 13 | 3% trimethylolpropane | 36.14 |
| 14 | 6% pentaerythritol | 43.4 |
| 15 | 3% pentaerythritol | 25.9 |
| 16 | 1% pentaerythritol | 17.15 |

The foregoing Examples demonstrate that the use of 1% of a hydrocarbyl polyol in preparing the prescribed zinc dialkyldithiophate of the invention results in the production of a zinc dialkyldithiophosphate with increased kinematic viscosity.

When higher amounts of the hydrocarbyl polyol are employed in the preparation of the prescribed zinc dialkyldithiophosphate dramatic increases in the viscosity of dialkyldithiophosphate are observed.

The prescribed zinc dialkyldithiophosphate of the invention was evaluated in a bench oxidation test. The test was conducted by effecting air oxidation of a mixture of the prescribed zinc dialkyldithiophosphate reaction product in a diluent oil containing an overbased calcium sulfonate. The test was conducted for 6 hours at 175° C. The difference or change in oxidation was measured by the growth of the carbonyl band at 1712 CM-1 in the IR. The differential IR (DIR) after 6 hours of oxidation was used as a measure of anti-oxidant activity. The lower the 6-hour DIR, the better the antioxidant activity. The oxidation test results are given in Table II below.

TABLE II

OXIDATION TEST RESULTS

| EXAMPLE | HYDROCARBYL POLYOL AND AMOUNT | 6 HOUR DIR |
|---|---|---|
| 2 (Comparative) | None | 3.71 |
| 3 | Bisphenol A - 1% | 3.10 |
| 4 | Glycerol - 1% | 3.06 |
| 5 | Ethyleneglycol - 1% | 3.19 |
| 6 | Ethyleneglycol - 3% | 3.15 |
| 7 | Ethyleneglycol - 4% | 3.24 |

The oxidation results show that the novel zinc dialkyldithiophosphate reaction products of the invention exhibited substantially improved oxidation as compared to a conventional zinc dialkyldithiophosphate (Comparative Example 2).

It is clear from Table II that all of the products modified with the diol polyol gave improved oxidation over the non-modified product (Example 2).

Low volatility in a zinc dialkyldithiophosphate (ZDTP) is desirable since the phosphorus in the zinc dialkyldithiophosphate (ZDTP) is known to poison the catalyst in the catalytic muffler. If the volatility of the zinc dialkyldithiophosphate (ZDTP) can be minimized, improved catalyst life should result.

Selected ZDPTs were evaluated for volatility characteristics in the ASTM D-1160 distillation test. The concentration of Zn and P was measured for the first 20% of the distillate. The lower the value for Zn and P, the lower the volatility of the ZDTP, and the better the volatility characteristics. Results are shown in Table III. It is clear from Table III that the diol modified material (D) has far superior volatility characteristics over the non-modified materials, both the primary (A) and secondary (B and C).

TABLE III

ASTM D-1160 DISTILLATION TEST[1]

| ZDTP | % P (X-RAY) | % Zn (X-RAY) |
|---|---|---|
| A (all primary ZDTP) | .25 | .078 |
| B (all secondary ZDTP) | .15 | .024 |
| C (all secondary ZDTP) | .12 | .027 |
| D (ETG-modified all secondary ZDTP | .02 | .011 |

[1]All additives (ZDTPs) were blended at 0.11 wt. % P in solvent neutral oil.

The foregoing examples demonstrate the surprisingly improved performance of the zinc dialkyldithiophosphates prepared by the novel process of this invention.

We claim:

1. A method for preparing a zinc dialkyldithiophosphate reaction product characterized by having improved volatility and reduced breakdown to sulfides properties which comprises reacting phosphorus pentasulfide with an aliphatic monohydric alcohol having from 3 to 10 carbon atoms in the presence of a glycol from the class consisting of ethylene glycol and glycerol and in which said glycol comprises from about 0.25 to 6 mole precent based on the total amount of alcohol employed to produce an intermediate dialkyldithiophosphoric acid reaction product, and reacting said intermediate with a basic zinc salt to produce said zinc dialkyldithiophosphate reaction product.

* * * * *